(12) United States Patent
Lloyd et al.

(10) Patent No.: US 7,671,231 B2
(45) Date of Patent: Mar. 2, 2010

(54) PROCESS FOR MAKING AMINO ACIDS

(76) Inventors: Michael C. Lloyd, 42 Woodlark Dr., Cottenham (GB) CB4 8XT; Edward D. Daugs, 2788 N. Tupelo Dr., Midland, MI (US) 48642; Cynthia L. Rand, 230 W. Barden Rd., Sanford, MI (US) 48657; Wei-Jun Peng, 3903 Morel Ct., Midland, MI (US) 48642

( * ) Notice: Subject to any disclaimer, the term of this patent is extended or adjusted under 35 U.S.C. 154(b) by 0 days.

(21) Appl. No.: 11/333,937

(22) Filed: Jan. 18, 2006

(65) Prior Publication Data
US 2007/0166806 A1    Jul. 19, 2007

(51) Int. Cl.
C07C 227/12    (2006.01)
(52) U.S. Cl. .................. 560/170; 435/106; 435/195
(58) Field of Classification Search ................ 435/106, 435/195
See application file for complete search history.

(56) References Cited

U.S. PATENT DOCUMENTS

| | | | |
|---|---|---|---|
| 4,668,651 A | 5/1987 | Billig et al. | |
| 6,174,711 B1* | 1/2001 | Tanaka et al. | 435/128 |
| 6,291,701 B1 | 9/2001 | Boesten et al. | |
| 6,570,033 B2 | 5/2003 | Rottger et al. | |
| 6,825,014 B2* | 11/2004 | Krimmer et al. | 435/106 |

FOREIGN PATENT DOCUMENTS

| | | |
|---|---|---|
| EP | 1 201 675 | 1/2004 |
| JP | 2003081963 | 3/2003 |
| JP | 2003081964 | 3/2003 |
| WO | WO 03/078444 | 9/2003 |

OTHER PUBLICATIONS

Gregory D Cuny and Stephen L Buchwald Practical, High-Yield, Regioselective, Rhodium-Catalyzed Hydroformylation of Functionalized alpha-Olefins J.Am.Chem.Soc. 1993, 115,2066-2068.*
Klein et al., "Highly Selective Catalyst Systems for the Hydrofomylation of Internal Olefins to Linear Aldehydes," *Angew. Chem. Int. Ed.*, 40 (18), pp. 3408-3411, 2001.
Selent et al., "New Phosphorus Ligands for the Rhodium-Catalyzed Isomerization/Hydroformylation of Internal Octenes," *Angew. Chem. Int. Ed.*, 40(9), pp. 1696-1698, 2001.
Cuny et al., "Practical, High-Yield, Regioselective, Rhodium-Catalyzed Hydroformylation of Functionalized α-Olefins," *J. Am. Chem. Soc.*, 115, pp. 2066-2068, 1993.

* cited by examiner

*Primary Examiner*—Brian J Davis

(57) ABSTRACT

A process for making an amino acid by the steps of: (a) contacting a compound of formula I

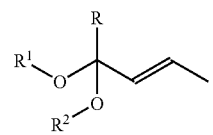

with a hydroformylation catalyst and synthesis gas to produce a mixture of aldehyde compounds comprising the formulas IIa, IIb and IIc;

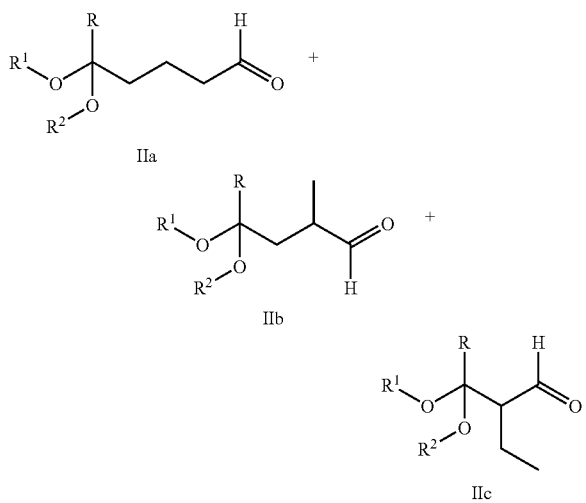

(b) reacting the mixture of aldehyde compounds from step (a) to produce a mixture of derivative compounds;
(c) contacting the mixture of derivative compounds from step (b) with an enantioselective hydrolase enzyme in the presence of water to produce an L-amino acid having the formula IV;

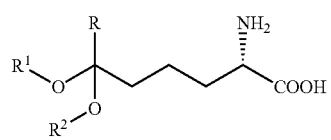

(d) isolating the amino acid having the formula IV in substantially pure form,
wherein in formulas I, IIa, IIb, IIc, IIIa, IIIb, IIIc and IV, R is H, alkyl or aryl and $R^1$ and $R^2$ are the same or different alkyl groups and wherein $R^1$ and $R^2$ may be fused.

25 Claims, No Drawings

PROCESS FOR MAKING AMINO ACIDS

FIELD OF THE INVENTION

The instant invention is in the field of methods for the synthesis of amino acids.

BACKGROUND OF THE INVENTION

L-amino acids, such as those having the formula IV,

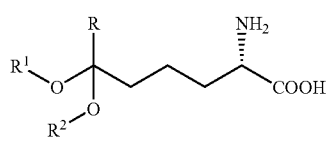

wherein R is H, alkyl or aryl and $R^1$ and $R^2$ are the same or different alkyl groups and wherein $R^1$ and $R^2$ may be fused, can be synthesized by using mono-acetal (ketal)-aldehydes. Synthesis of mono-acetal-aldehydes from dialdehydes suffers from complications in purification and low yields, particularly when the two formyl groups are equivalent. It is even more difficult to make ketal-aldehydes from ketoaldehydes because the formyl group is more reactive than the keto group. Hydroformylation of readily available olefinic acetals or olefinic ketals typically produces a desired linear aldehyde and undesired branched aldehydes. Separation of the linear mono-acetal aldehyde and the branched mono-acetal-aldehydes is generally very difficult due to high, similar boiling points.

SUMMARY OF THE INVENTION

We have discovered that it is not necessary to separate the branched aldehydes from the linear aldehyde if, for example, a subsequent formation of a masked amino acid derivative and catalytic bio-resolution steps are used to convert the linear aldehyde selectively to the desired final product. The masked amino acid derivative may be selected from the group consisting of amino nitrile, N-acyl amino acid, amino amide, hydantoin and amino ester. The catalytic bio-resolution may be effected by exposure of said derivative to an enantioselective hydrolase enzyme selected from the group consisting of nitrilases, nitrilase hydratases, aminoacylases, amidases, hydantionases, esterases and other hydrolase enzymes having equivalent activity to the aforementioned.

In general, the instant invention is process for making an amino acid, comprising the steps of: (a) contacting a compound of formula I

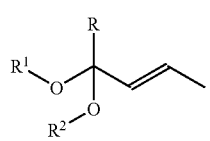

with a hydroformylation catalyst and synthesis gas to produce a mixture of aldehyde compounds comprising the formulas IIa, IIb and IIc;

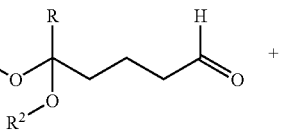

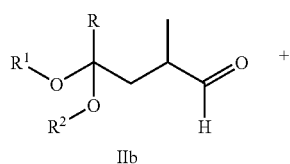

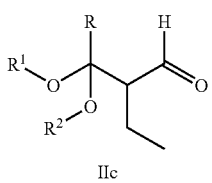

(b) reacting the mixture of aldehyde compounds from step (a) to produce a mixture of derivative compounds;

(c) contacting the mixture of derivative compounds from step (b) with an enantioselective hydrolase enzyme in the presence of water to produce an L-amino acid having the formula IV;

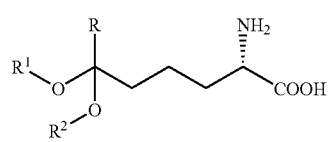

(d) isolating the amino acid having the formula IV in substantially pure form, wherein in formulas I, IIa, IIb, IIc, IIIa, IIIb, IIIc and IV, R is H, alkyl or aryl and $R^1$ and $R^2$ are the same or different alkyl groups and wherein $R^1$ and $R^2$ may be fused.

In one embodiment, the instant invention is a process for making an amino acid, comprising the steps of: (a) contacting a compound of formula I

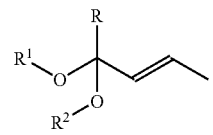

with a hydroformylation catalyst and synthesis gas to produce a mixture of aldehyde compounds comprising the formulas IIa, IIb and IIc;

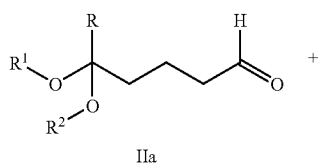

IIa

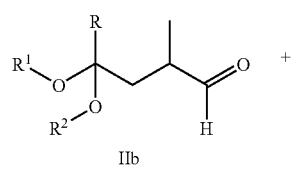

IIb

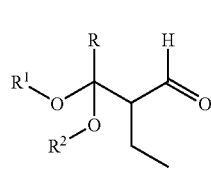

IIc (b) contacting the mixture of aldehyde compounds with a Strecker reagent to produce a mixture of nitrile compounds comprising the formulas IIIa, IIIb and IIIc; and

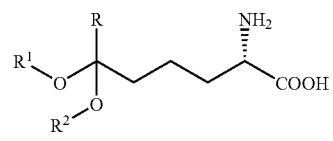

IIIa

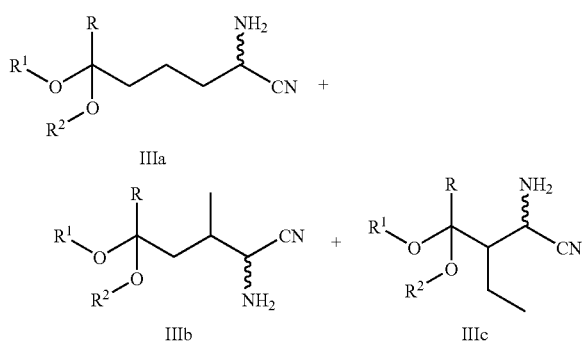

IIIb                    IIIc (c) contacting the mixture of nitrile compounds with an L-specific nitrilase in the presence of water to produce an L-amino acid having the formula IV, and

IV (d) isolating, preferably by precipitation, the L-amino acid having the formula IV, in substantially pure form, wherein in formulas I, IIa, IIb, IIc, IIIa, IIIb, IIIc and IV, R is H, alkyl or aryl and $R^1$ and $R^2$ are the same or different alkyl groups and wherein $R^1$ and $R^2$ may be fused.

In another embodiment, the instant invention is a process for making an amino acid, composing the steps of: (a) contacting a compound of formula I

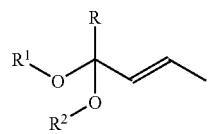

I with a hydroformylation catalyst and synthesis gas to produce a mixture of aldehyde compounds comprising the formulas IIa, IIb and IIc;

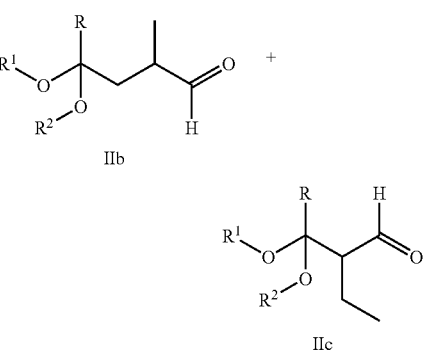

IIa

IIb

IIc (b) contacting the mixture of aldehyde compounds with a Strecker reagent to produce a mixture of nitrile compounds comprising the formulas IIIa, IIIb and IIIc;

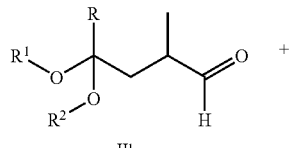

IIIa

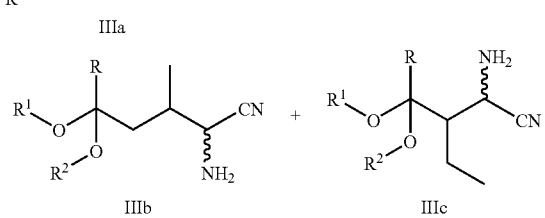

IIIb                    IIIc further contacting the mixture of nitrile compounds with aqueous ethanol under basic conditions to produce a mixture of amino acid salts comprising the formulas Va, Vb, Vc;

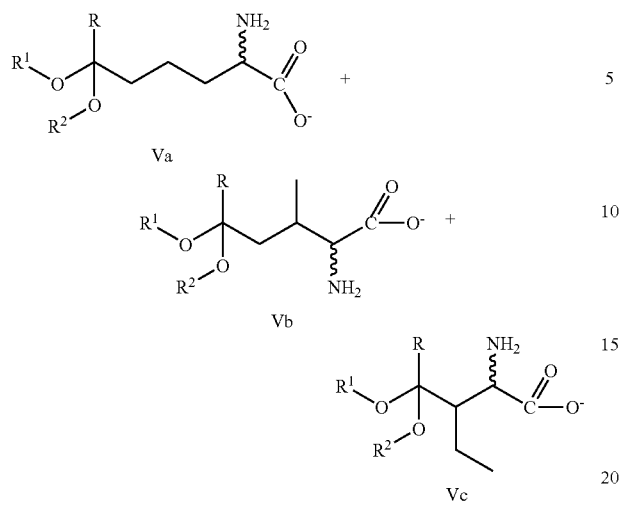

further comprising the mixture of amino acid salts with an acylating reagent to produce an acetal compound comprising the formula VIa; and

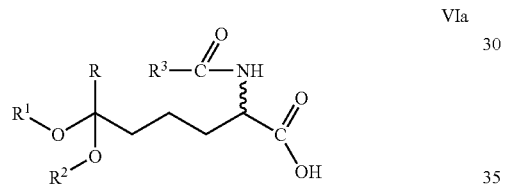

(c) contacting the acetal compound with an L-specific N-acylase in the presence of water to produce an L-amino acid having the formula IV, and

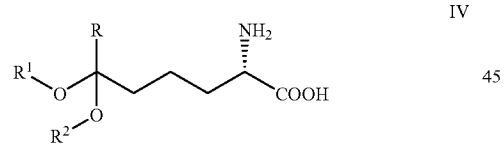

(d) isolating, preferably by precipitation, the L-amino acid having the formula IV, in substantially pure form, wherein in formulas I, IIa, IIb, IIc, IIIa, IIIb, IIIc, Va, Vb, Vc, VIa and IV, R is H, alkyl or aryl, wherein $R^3$ is an alkyl, aryl or alkaryl group containing from one to ten carbons and wherein $R^1$ and $R^2$ are the same or different alkyl groups and wherein $R^1$ and $R^2$ may be fused.

In another embodiment of the instant invention, the mixture of aldehyde compounds IIa, IIb and IIc can be further reacted such that linear aldehyde IIa is converted to a masked amino acid derivative selected from an amino amide having the formula VIIa, a hydantoin having the formula VIIIa or an amino ester having the formula IXa, wherein $R^3$ is an alkyl, aryl or alkaryl group containing from one to ten carbons and wherein $R^1$ and $R^2$ are the same or different alkyl groups and wherein $R^1$ and $R^2$ may be fused. Such derivative is then subject to enantioselective catalytic bio-resolution to produce the L-amino acid of formula IV which is then isolated, preferably by precipitation, to produce purified L-amino acid of formula IV.

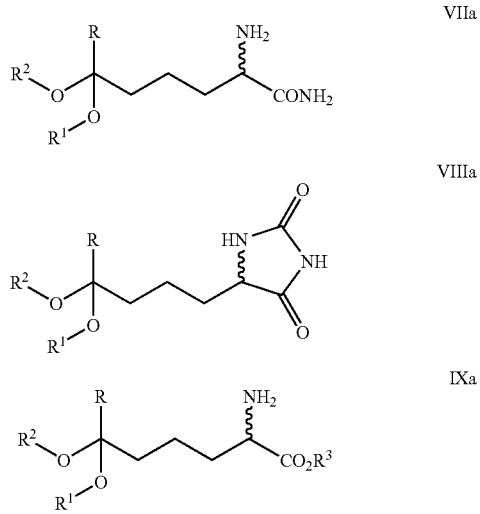

DETAILED DESCRIPTION

The instant invention in one embodiment is a process for making an L-amino acid having the formula IV, wherein R is H, alkyl or aryl and $R^1$ and $R^2$ are the same or different alkyl groups and wherein $R^1$ and $R^2$ may be fused.

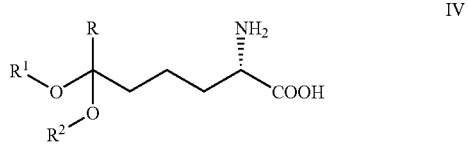

L-amino acids having the formula IV are suited for use as intermediates in the pharmaceutical industry.

The process of the instant invention comprises four steps. The first step is to contact a compound of formula I

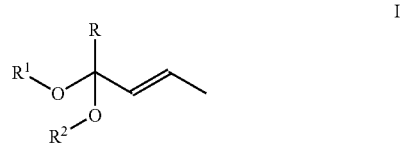

with a hydroformylation catalyst and syntheses gas to produce a mixture of aldehyde compounds comprising the formulas IIa, IIb and IIc (and may contain small amounts of other by products, such as from hydrogenation and aldol condensation), wherein R is H, alkyl or aryl and $R^1$ and $R^2$ are the same or different alkyl groups and wherein $R^1$ and $R^2$ may be fused.

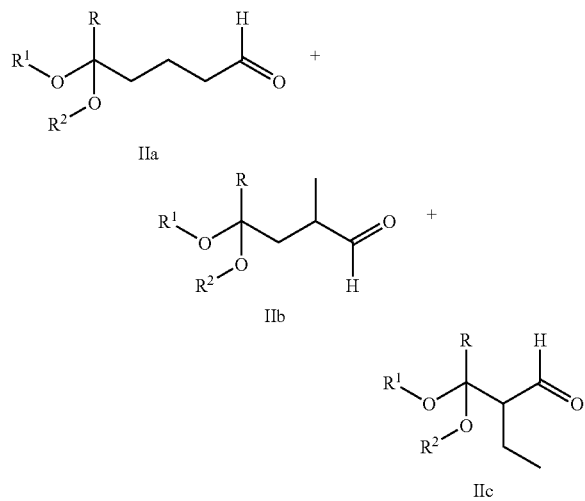

Hydroformylation of olefins to aldehydes using synthesis gas is well known, see, for example, Klein et al., Angrew. Chem. Int. Ed. 2001, 40, No. 18, 3408-3411. In the instant invention, the synthesis gas is preferably comprises hydrogen and carbon monoxide in a mole ratio of about 2:1 to 1:2. Although the specific hydroformylation catalyst used is not critical in the instant invention (see for example, the hydroformylation catalyst of Cuny et al., J. Am. Chem. Soc. 1993 2066-2068 or Selent et al., Ang. Chem. Int. Ed. 2001, 40, No. 9, 1696-1698), preferably, the hydroformylation catalyst is sufficient selective to maximize the production of the linear aldehyde of formula IIa relative to the branched aldehydes of formulas IIb and IIc. More specifically, the hydroformylation catalyst selected for use in the instant invention preferably results in a mole ratio of compound of formula IIa to the compounds of formula IIb and IIc of at least 3:1. The hydroformylation catalyst selected for use in the instant invention more preferably results in a mole ratio of compound of formula IIa to the compounds of formula IIb and IIc of at least 6:1. The hydroformylation catalyst selected for use in the instant invention even more preferably results in a mole ratio of compound of formula IIa to the compounds of formula IIb and IIc of at least 9:1.

WO 03/078444 A2 and U.S. Pat. No. 4,668,651 teache several highly preferred hydroformylation catalysts suitable for use in the instant invention specifically including a rhodium/biphenphos hydroformylation catalyst which will be described below in greater detail.

The hydroformylation reaction is preferably carried out in an aprotic polar solvent such as tetrahydrofuran. Then, a nonpolar solvent such as hexane is preferably added to the reaction mixture to form a mixture of the aldehyde compounds IIa, IIb and IIc in a mixture comprising the aprotic polar solvent and the nonpolar solvent. In this preferred embodiment, the mixture is then extracted with water to form an aqueous phase comprising the mixture of aldehyde compounds IIa, IIb and IIc and the aprotic polar solvent and an organic phase comprising the hydroformylation catalyst and the nonpolar solvent so that the hydroformylation catalyst can be separated from the mixture of aldehyde compounds.

The specific aprotic polar solvent used for the hydroformylation reaction of the instant invention is not critical. However, preferably the aprotic polar solvent has an aqueous-hexane partition coefficient in the range of from 8:1 to 1:2, and more preferably in the range of from 4:1 to 1:1 (and most preferably about 2:1). The solvent can, preferably, be easily evaporated from the aqueous product mixture. The temperature of the hydroformylation reaction of the instant invention is preferably in the range of from 30 to 120 degrees Celsius, and more preferably in the range of from 40 to 100 degrees Celsius, and most preferably in the range of from 50 to 90 degrees Celsius. The synthesis gas used preferably has a carbon monoxide (CO) to hydrogen ($H_2$) mole ratio of 1:1. The pressure of the synthesis gas used in the hydroformylation reaction is preferably in the range of from 1 to 200 pounds per square inch gauge pressure (psig), and more preferably in the range of from 5 to 100 psig, and most preferably in the range of from 10-50 psig.

The aqueous solution of the aldehydes compounds comprising formulas IIa, IIb, and IIc can be used directly in the subsequent Strecker reaction as described hereinbelow. Alternatively, the aldehyde compounds IIa, IIb and IIc in the aqueous phase are then preferably extracted from the aqueous phase with a volatile solvent, for example, methylene chloride which is then dried with, for example, magnesium sulfate, followed by evaporation of the volatile solvent to yield a product which comprises the aldehyde compounds IIa, IIb and IIc. The mixture of aldehyde compounds comprising the formulas IIa, IIb and IIc is preferably analyzed by gas chromatography/mass spectroscopy (GCMS).

The mixture of aldehyde compounds is then contacted with a Strecker reagent to produce a mixture of nitrile compounds comprising the formulas IIIa, IIIb and IIIc.

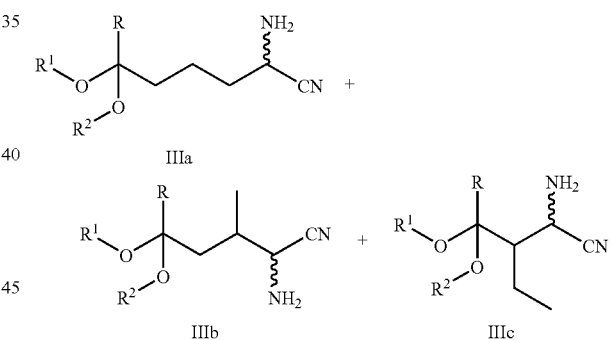

The specific Strecker reagent used is not critical in the instant invention. However, a Strecker reagent comprised of potassium cyanide or sodium cyanide, ammonium chloride, ammonium hydroxide and water is preferred and such a reagent will be described below in greater detail. Within this preferred embodiment, the Strecker reagent is normally combined with the mixture of aldehyde compounds at about 0° C. or lower and then the reaction mixture allowed to warm to about ambient temperature in order to complete the reaction. The nitrile compounds IIIa, IIIb and IIIc are then preferably extracted with a volatile solvent, such as ethyl acetate. This extract is then dried with a drying agent, such as magnesium sulfate, and then the volatile solvent is preferably evaporated to produce a product comprising the nitrile compounds IIIa, IIIb and IIIc. The mixture of nitrile compounds comprising the formulas IIIa, IIIb and IIIc is preferably analyzed by gas chromatography/mass spectroscopy (GCMS).

According to one embodiment, the mixture of nitrile compounds IIIa, IIIb and IIIc is then contacted with an L-specific nitrilase to produce an L-amino acid having the formula IV, wherein R is H, alkyl or aryl and $R^1$ and $R^2$ are the same or different alkyl groups and wherein $R^1$ and $R^2$ may be fused. The L-amino acid having the formula IV is preferably assayed by chiral HPLC.

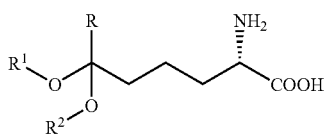

IV

When 1,3-dioxolane-2-butanal is the compound of formula IIa, then L-allysine ethylene acetal is the compound of formula IV. This reaction preferably occurs at or near ambient temperatures (preferably about 10-40° C., more preferably about 15-30° C.). The pH is controlled as appropriate for the enzyme and preferably is maintained at about pH 7-8. To achieve favorable process economics, substrate concentration is preferably at least 50 g/L and more preferably at least 100 g/L. To achieve such substrate concentrations, a water miscible co-solvent may be required, preferably methanol or alternatively ethanol, tetrahydrofuran, 1,2-dimethoxyethane or 1,4-dioxane.

The specific L-specific nitrilase used is not critical in the instant invention. An important benefit of the instant invention is the fact that L-specific nitrilase will not react with the nitrile compounds IIIb or IIIc or the D isomer of the nitrile compound IIIa. In addition, the solubility of the L-amino acid IV produced is generally relatively low in the buffers used for the nitrilase so that the L-amino acid IV conveniently precipitates from solution in a high purity crystalline form.

As an alternative embodiment of the instant invention, the mixture of nitrile compounds IIIa, IIIb and IIIc can be contacted with aqueous ethanol (or another water miscible solvent such as methanol, ethanol, tetrahydrofuran, 1,2-dimethoxyethane or 1,4-dioxane) under basic conditions to produce a mixture of amino acid salts comprising the formulas Va, Vb and Vc. Preferably, the reaction mixture is heated at or near reflux temperatures. The mixture of amino acid salts comprising the formulas Va, Vb and Vc is preferably analyzed by high performance liquid chromatography (HPLC).

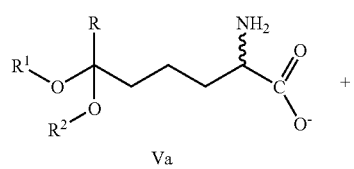

Va

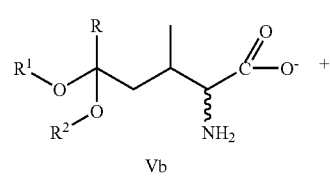

Vb

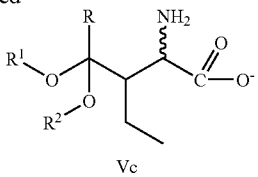

Vc

The mixture of amino acid salts can then be contacted with an acylating reagent, such as acetic anhydride or benzoyl chloride, to produce an acetal compound comprising the formula VIa. The acetal compound is then preferably extracted with a volatile solvent, such as ethyl acetate. This extract is then dried with a drying agent, such as magnesium sulfate, and then the volatile solvent is preferably evaporated to produce a product comprising the acetal compound VIa. The acetal compound comprising the formula VIa is preferably analyzed by high performance liquid chromatography (HPLC).

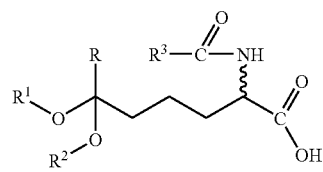

VIa

The acetal compound is then be contacted with an L-specific N-acylase to produce the L-amino acid having the formula IV, wherein, again, R is H, alkyl or aryl, wherein $R^3$ is an alkyl, aryl or alkaryl group containing from one to ten carbons, and $R^1$ and $R^2$ are the same or different alkyl groups and wherein $R^1$ and $R^2$ may be fused.

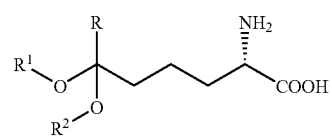

IV

When the mixture of amino acid salts is contacted with the acylating reagent a mixture of acetal compounds comprising the formulas VIa, VIb and VIc are produced.

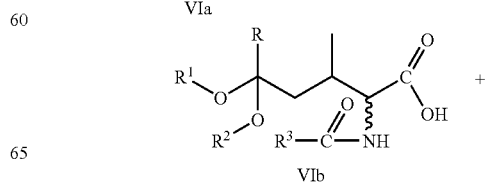

VIa

VIb

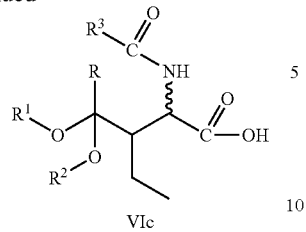

VIc

The mixture of acetal compounds are then preferably extracted with a volatile solvent, such as ethyl acetate. This extract is then dried with a drying agent, such as magnesium sulfate, and then the volatile solvent is preferably evaporated to produce a product comprising the acetal compounds VIa, VIb and VIc. The acetal compounds comprising the formulas VIa, VIb and VIc are preferably analyzed by high performance liquid chromatography (HPLC).

When the mixture of acetal compounds VIa, VIb and VIc forms a precipitate, then it is preferable to wash such precipitate with a solvent (such as methyl t-butyl ether) to dissolve compounds VIb and VIc from VIa, thereby leaving compound VIa in pure or purer form for contact with the L-specific N-acylase.

The specific L-specific N-acylase used is not critical in the instant invention. Preferably a thermophilic N-acylase is used, allowing operating temperatures of about 40-70° C. and thereby achieving faster reaction and/or higher substrate concentration of substrate. A conventional N-acylase may also be employed at typical operating temperatures of about 15-45° C. For both thermophilic and conventional N-acylases, stringent pH control during the reaction is not required although a starting pH in the range 6-9 is preferred. Also, substrate concentration is preferably at least 50 g/L and more preferably at least 100 g/L. An important benefit of the instant invention is the fact that L-specific N-Nacylase will not react with any acetal compounds VIb or VIc or the D isomer of compound VIa. In addition, the solubility of the L-amino acid IV produced is generally relatively low in the buffers used for the acylase so that the L-amino acid IV conveniently precipitates from solution in a high purity crystalline form. The L-amino acid having the formula IV is preferably assayed by chiral HPLC.

As alternative embodiments of the instant invention, the mixture of aldehyde compounds IIa, IIb and IIc, obtained by hydroformylation, can be further reacted such that linear aldehyde IIa is converted to a masked amino acid derivative selected from an amino amide having the formula VIIa, a hydantoin having the formula VIIIa or an amino ester having the formula IXa. Such derivative is then subject to enantioselective catalytic bio-resolution. L-Selective amidases effective in the enantioselective hydrolysis of amino amide VIIa at about pH 9-10 are reported in U.S. Pat. Nos. 6,174,711 and 6,291,701, incorporated herein by reference. L-Selective hydantoinases, effective in the enantioselective hydrolysis of hydantoin VIIa and typically used in conjunction with a carbamoylase or equivalent enzyme are reported in U.S. Pat. No. 6,825,014, incorporated herein by reference. None of the patents U.S. Pat. Nos. 6,174,711, 6,291,701 or 6,825,014 report hydroformylation as a process used to prepare bio-resolution substrates.

VIIa

VIIIa

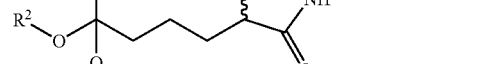

IXa

Although the preferred means of isolating the L-amino acid of formula IV in relatively pure form is by precipitation, it should be understood that other means of isolation can be used such as evaporation, chromatography and extraction.

EXAMPLE 1

The following reaction scheme (wherein Ha-Hf defines different substitution positions for hydrogen) summarizes the hydroformylation of the compound of formula I shown below on left to produce a product comprising a mixture of aldehydes and other products.

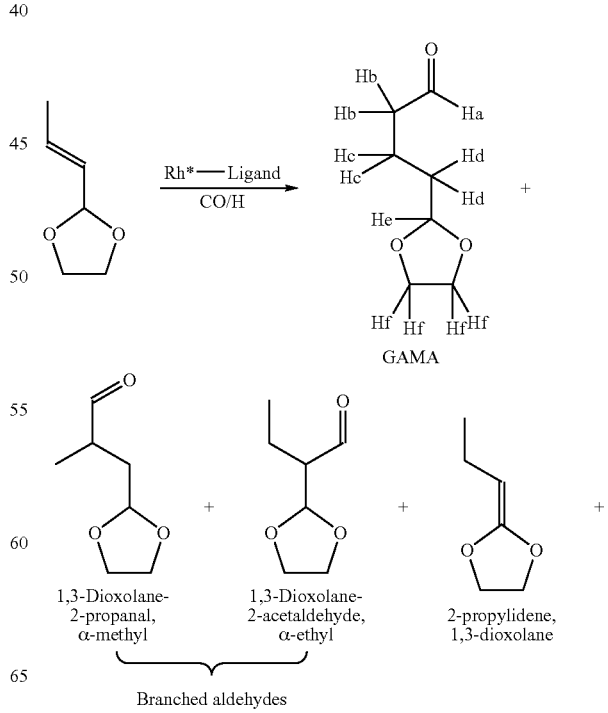

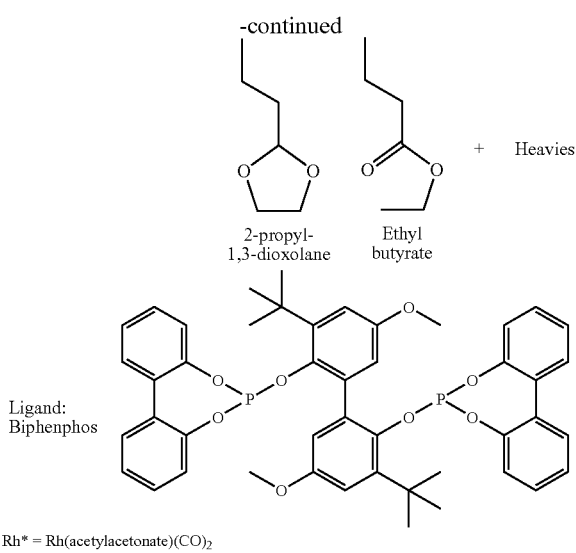

A hydroformylation catalyst solution is prepared in a glove box by dissolving 0.578 grams of Biphenos and 0.0978 grams of rhodium compound in 10 grams of tetrahydrofuran (THF) in a flask, which is then sealed with a septum. A feed of 93.04 grams of the compound of formula I shown in the preceding reaction scheme on left, 80 grams of THF and 8.09 grams of toluene is weighed out in the glove box. The catalyst solution is transferred into a 300 ml stirred Parr reactor under nitrogen. The nitrogen is purged from the reactor by pressurizing and venting 1:1 mole ratio $CO:H_2$ syn gas three times. The feed solution was transferred into a sample cylinder attached to the reactor and purged by pressurizing and venting 1:1 mole ratio $CO:H_2$ syn gas three times. The feed was added into the reactor when the reactor is heated to 85 degrees Celsius. The temperature of the reactor is controlled at 85 degrees Celsius. The pressure of syn gas in the reactor is controlled at 25 psig. After 7 hours, GC analysis showed 91% conversion of the compound of formula I shown in the preceding reaction scheme on left and 79% yield of GAMA.

About 75 milliliters of hexane is mixed with the reaction solution and this mixture is then extracted with degassed and deionized water (3×120 milliliters). The aqueous extract is then extracted with methylene chloride (5×120 milliliters). The methylene chloride extract is dried with $MgSO_4$ and filtered. After evaporating the methylene chloride, the neat product comprising the mixture of aldehydes is analyzed by GCMS and is found to contain GAMA (89.0 wt %), branched aldehydes (4.7 wt %) and heavies (2.6 wt %). The final isolated yield for GAMA is about 70%.

Into a 3-neck 100 milliliter round bottom flask is placed 743 milligrams (13.9 mmol) of ammonium chloride, 904 milligrams (13.9 mmol) of potassium cyanide, 18 milliliters of water and 16 milliliters of 35% aqueous ammonia. The solution is stirred under a nitrogen atmosphere and cooled to below zero degrees Celsius by means of a salt ice bath. To the cooled solution is slowly added over a ten minutes the above detailed product comprising the mixture of aldehydes, taking care that the temperature remains below 0° C. After the addition is complete, the reaction mixture is allowed to slowly warm up to room temperature and left stirring overnight. After overnight stirring the reaction is halted and extracted with 3×30 milliliters of ethyl acetate. The combined ethyl acetate extract is then dried over magnesium sulphate and the ethyl acetate evaporated under reduced pressure to yield a mixture comprising the acetal-aminonitriles.

Into a 25 ml round bottom flask is placed 500 milligrams of the mixture comprising the acetal-aminonitriles in 1 ml methanol and 9 ml of distilled water. The pH of the stirred solution is adjusted to 7 by dropwise addition of 1M hydrochloric acid solution. Then 27 milligrams of nitrilase NIT-7478 (Diversa, lot 4556) is added. The reaction mixture is stirred for 43 hours at ambient temperature, during which time the pH is maintained between 7 and 8 by further dropwise additions of 1M hydrochloric acid solution. The reaction is then halted and the reaction mixture is concentrated to dryness under reduced pressure. The resulting residue is washed with 10 milliliters of ethyl acetate and the insoluble amino acid is recovered by filtration and dried in a vacuum oven to yield a white solid. Chiral HPLC analysis (penicillamine column) indicates an L-allysine acetal purity of 98.8% and an overall mole percent yield (based on moles of the compound of formula I shown in the preceding reaction scheme on left starting material) of about 30%.

EXAMPLE 2

This example starts with the aminonitrile mixture of Example 1. Into a 50 ml round bottom flask is placed 725 milligrams of the aminonitrile mixture in 20 milliliters of 50% aqueous ethanol, together with 720 milligrams (18 mmol, 4.2 eq) of sodium hydroxide. The reaction mixture is stirred continuously and heated under refluxing conditions for 4 hours. After this time the mixture is cooled to below 5° C. by means of a salt-ice bath and 490 microliters (5.11 mmol, 1.2 eq) of acetic anhydride is added to the stirred solution. The reaction mixture is allowed to warm up to room temperature and left stirring overnight. The mixture is then acidified to pH 3 with 6M HCl solution and extracted with 3×50 milliliters of ethyl acetate. The combined extracts are dried over magnesium sulphate and the ehyl acetate is evaporated under reduced pressure to yield an orange oil containing about 500 milligrams of N—Ac allysine acetal as determined by GCMS.

Into a 50 ml jacketed vessel is placed the above detailed orange oil comprising the N—Ac allysine acetal dissolved in 20 ml of distilled water. The solution is continuously stirred, heated to 60 degrees Celsius and the pH of the solution is adjusted to 7 by dropwise addition of 1M NaOH solution. 1 milliliter of L-acylase solution is then added and the mixture is left stirring for 24 hours at 60° C. The reaction mixture is then acidified to pH 3 with 6M HCl solution and extracted with 3×25 milliliters of ethyl acetate in order to remove the residual N—Ac allysine acetal. The pH of the aqueous phase is readjusted to 7.3 using 5M sodium hydroxide solution, concentrated to one quarter volume and diluted with 20 milliliters of isopropanol. The resulting white precipitate is recovered by filtration and dried overnight in a vacuum oven, yielding 150 milligrams of L allysine acetal. Chiral HPLC analysis (penicillamine column) indicates an L-allysine acetal purity of 99%.

EXAMPLE 3

This example also starts with an aminonitrile mixture made according to the teachings of Example 1. Into a 250 ml round bottom flask is placed ten grams of the aminonitrile mixture in 120 ml of 50% aqueous ethanol, together with 10.54 grams (264 mmol, 4 eq) of sodium hydroxide. The reaction mixture is stirred continuously and heated under refluxing conditions for 5 hours. After this time the mixture is allowed to cool to room temperature and ethanol is removed under reduced pressure. The aqueous solution is then cooled to below 5° C. by means of a salt-ice bath and a solution of 9.18 milliliters (79 mmol, 1.2 eq) of benzoyl chloride in 15 ml THF is slowly added to the stirred solution. The reaction mixture is allowed to warm up to room temperature and left stirring overnight. After 20 hours, the mixture is acidified to pH 3 with 6M HCl solution and extracted with 3×75 milliliters of ethyl acetate. The combined extracts are dried over magnesium sulphate and concentrated under reduced pressure to yield an off white solid. This material is contaminated with benzoic acid and is purified by slurrying in methyl t-butyl ether (MTBE). The product comprises N-benzoyl allysine and is recovered by filtration and dried in a vacuum oven to yield an off white solid.

Into a 1 liter jacketed vessel is placed 48.4 grams of the above-detailed off white solid. The vessel was heated to 65° C. and a solution of 470 milliliters of distilled water and 10 milliliters of 48% sodium hydroxide solution is added to the stirred vessel. The pH of the solution was adjusted to 7.5 by addition of a few drops of 48% NaOH solution. Twelve milliliters of L-acylase solution (31800 Units) is then added and the mixture is left stirring for 18 hours at 65° C. The reaction mixture is filtered to remove any precipitated protein and the filtrate is concentrated under reduced pressure to approximately one third volume. The pH of the concentrated solution is adjusted to 7.4 using 5M sodium hydroxide solution and two volumes of ethanol were added. The mixture is cooled to below 10° C. and left to stand for 1 hour. The precipitate is recovered by cold filtration, washed with further cold ethanol and dried overnight in a vacuum oven, yielding 12.3 g of L-allysine acetal as a white crystalline solid. Chiral HPLC analysis (penicillamine column) indicates an L-allysine acetal purity of better than 99%.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A process for making an amino acid, comprising the steps of: (a) contacting a compound of formula I

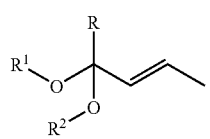

with a hydroformylation catalyst and synthesis gas to produce a mixture of aldehyde compounds comprising the formulas IIa, IIb and IIc;

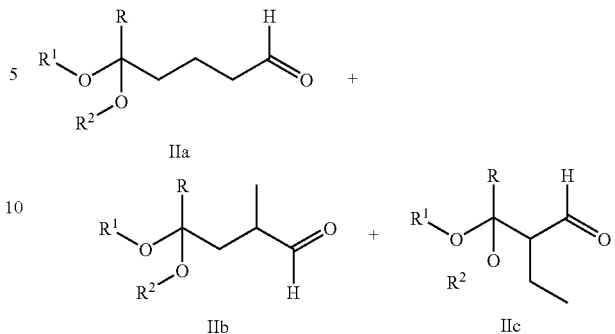

(b) reacting the mixture of aldehyde compounds from step (a) to produce a mixture of derivative compounds;
(c) contacting the mixture of derivative compounds from step (b) with an enantioselective hydrolase enzyme in the presence of water to produce an L-amino acid having the formula IV;

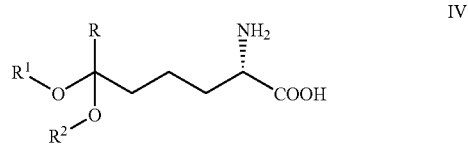

(d) isolating the amino acid having the formula IV, wherein in formulas I, IIa, IIb, IIc, and IV, R is H, alkyl or aryl and $R^1$ and $R^2$ are the same or different alkyl groups and wherein $R^1$ and $R^2$ may be fused.

2. The process of claim 1, wherein the mixture of derivative compounds of step (b) comprises a masked amino acid derivative selected from the group consisting of amino nitrile, N-acyl amino acid, amino amide, hydantoin and amino ester.

3. The process of claim 1, wherein the enantioselective hydrolase enzyme of step (c) is selected from the group consisting of nitrilases, nitrilase hydratases, aminoacylases, amidases, hydantionases, and esterases.

4. The process of claim 1, wherein the isolation of step (d) comprises precipitation.

5. The process of claim 1, wherein step (b) comprises contacting the mixture of aldehyde compounds with a Strecker reagent to produce a mixture of nitrile compounds comprising the formulas IIIa, IIIb and IIIc; and

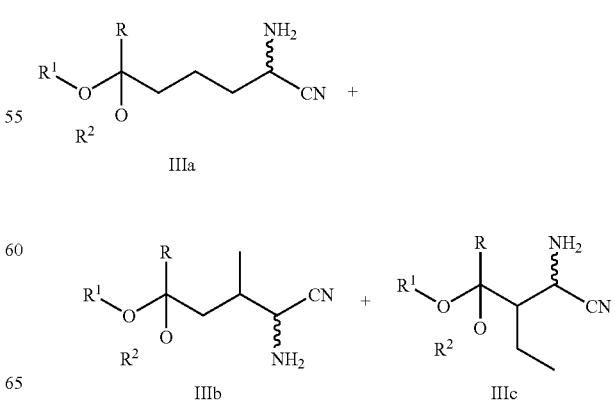

step (c) comprises contacting the mixture of nitrile compounds with an L-specific nitrilase to produce an L-amino acid having the formula IV,

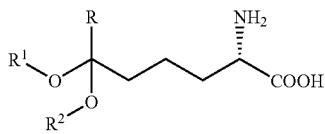

IV wherein in formulas IIIa, IIIb, and IIIc, R is H, alkyl or aryl and $R^1$ and $R^2$ are the same or different alkyl groups and wherein $R^1$ and $R^2$ may be fused.

6. The process of claim 1, wherein step (a) is carried out in an aprotic polar solvent, wherein between steps (a) and (b) a nonpolar solvent is added to the mixture of aldehyde compounds to form a mixture of aldehyde compounds in a mixture comprising the aprotic polar solvent and the nonpolar solvent which mixture is then extracted with water to form an aqueous phase comprising the mixture of aldehyde compounds and the aprotic polar solvent and an organic phase comprising the hydroformylation catalyst and the nonpolar solvent so that the hydroformylation catalyst can be separated from the mixture of aldehyde compounds.

7. The process of claim 6, wherein the aprotic polar solvent comprises tetrahydrofuran.

8. The process of claim 6, wherein the nonpolar solvent comprises an alkane.

9. The process of claim 6, wherein the aprotic polar solvent is tetrahydrofuran and wherein the nonpolar solvent is hexane.

10. The process of claim 9, wherein the compound of formula I is 2-(prop-1-enyl)-1,3-dioxolane and wherein the compound of formula IV is L-allysine acetal.

11. The process of claim 10, wherein the hydroformylation catalyst comprises ruthenium/biphenphos.

12. The process of claim 6, wherein the aprotic polar solvent has an aqueous-hexane partition coefficient in the range of from 8:1 to 1:2.

13. A process according to claim 1, wherein step (b) comprises contacting the mixture of aldehyde compounds with a Strecker reagent to produce a mixture of nitrile compounds comprising the formulas IIIa. IIIb and IIIc:

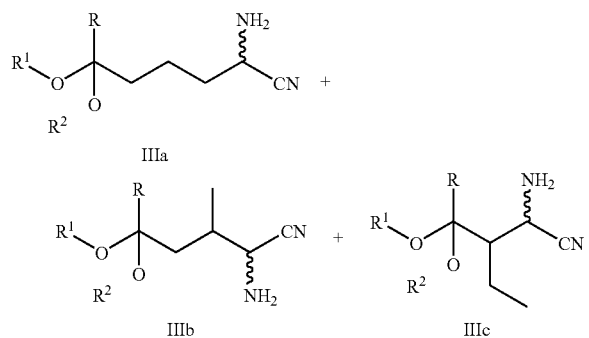

and further comprises contacting the mixture of nitrile compounds with aqueous ethanol under basic conditions to produce a mixture of amino acid salts comprising the formulas Va, Vb and Vc:

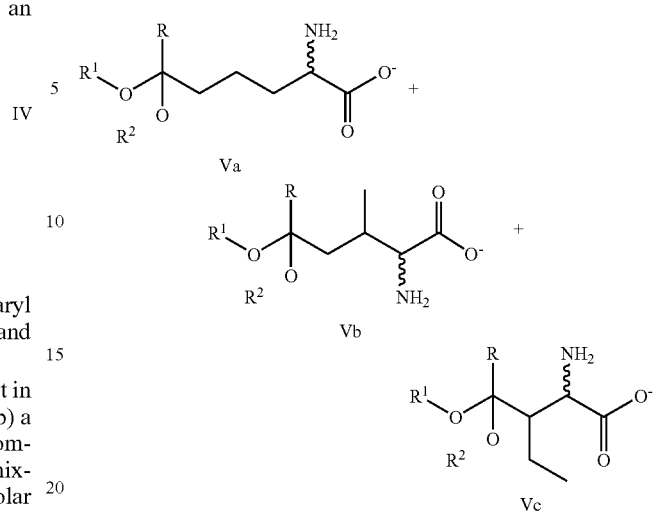

and further comprises contacting the mixture of amino acid salts with an acylating reagent to produce an acetal compound comprising the formula VIa; and

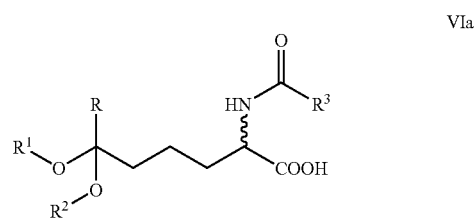

step (c) comprises contacting the acetal compound with an L-specific N-acylase to produce an L-amino acid having the formula IV,

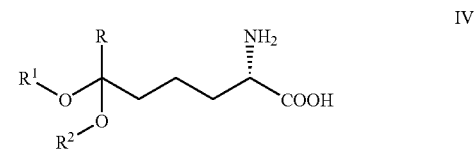

IV wherein in formulas IIIa, IIIb, IIIc, Va, Vb, Vc, and VIa, R is H, alkyl or aryl, wherein $R^3$ is an alkyl, aryl or alkaryl group containing from one to ten carbons and wherein $R^1$ and $R^2$ are the same or different alkyl groups and wherein $R^1$ and $R^2$ may be fused.

14. The process of claim 13, wherein step (a) is carried out in an aprotic polar solvent, wherein between steps (a) and (b) a nonpolar solvent is added to the mixture of aldehyde compounds to form a mixture of aldehyde compounds in a mixture comprising the aprotic polar solvent and the nonpolar solvent which mixture is then extracted with water to form an aqueous phase comprising the mixture of aldehyde compounds and the aprotic polar solvent and an organic phase comprising the hydroformylation catalyst and the nonpolar solvent so that the hydroformytation catalyst can be separated from the mixture of aldehyde compounds.

15. The process of claim 11, wherein the aprotic polar solvent comprises tetrahydrofuran.

16. The process of claim 14, wherein the nonpolar solvent comprises an alkane.

17. The process of claim 14, wherein the aprotic polar solvent is tetrahydrofuran and wherein the nonpolar solvent is hexane.

18. The process of claim 17, wherein the compound of formula I is 2-(prop-1-enyl)-1,3-dioxolane and wherein the compound of formula IV is L-allysine acetal.

19. The process of claim 18, wherein the hydroformylation catalyst comprises ruthenium/biphenphos.

20. The process of claim 14, wherein the aprotic polar solvent has an aqueous-hexane partition coefficient in the range of from 8:1 to 1:2.

21. The process of claim 13, wherein in step (b) a mixture of acetal compounds is produced comprising the formula VIa, VIb and VIc;

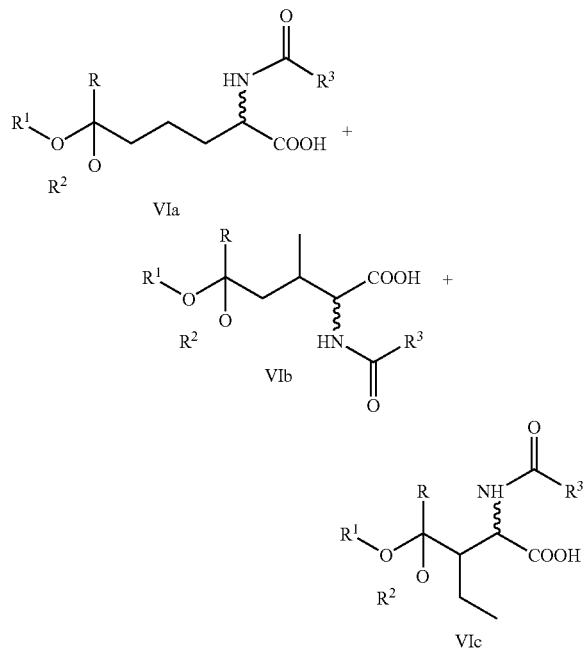

wherein in step (c) the mixture of acetal compounds is contacted with the L-specific N-acylase to produce the L-amino acid having the formula IV, and wherein in formulas VIb and VIc R is H, alkyl or aryl, wherein $R^3$ is an alkyl, aryl or alkaryl group containing from one to ten carbons and wherein $R^1$ and $R^2$ are the same or different alkyl groups and wherein $R^1$ and $R^2$ may be fused.

22. The process of claim 2, wherein the mixture of derivative compounds of step (b) comprises a compound of formula VIIa, VIIIa or IXa

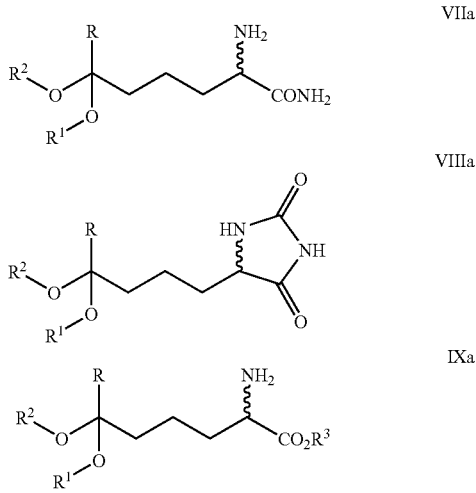

where R is H, alkyl or aryl and $R^1$ and $R^2$ are the same or different alkyl groups and where $R^3$ is an alkyl, aryl or alkaryl group containing from one to ten carbons.

23. The process of claim 1, wherein the mixture of derivative compounds of step (b) comprises a masked amino acid derivative selected from the group consisting of amino nitrile, N-acyl amino acid, amino amide, and amino ester.

24. The process of claim 1, wherein the enantioselective hydrolase enzyme of step (c) is selected from the group consisting of nitrilases, nitrilase hydratases, aminoacylases, amidases, and esterases.

25. The process of claim 1, wherein the enantioselective hydrolase enzyme of step (c) is selected from the group consisting of nitrilases and aminoacylases.

* * * * *